United States Patent
Xin (10) Patent No.: US 11,089,973 B2
(45) Date of Patent: Aug. 17, 2021

(54) METHOD FOR SOLVING ELECTRICAL PROPERTY DISTRIBUTION AND LOCAL SPECIFIC ABSORPTION RATE OF TISSUE FROM VIEW OF ELECTROMAGNETIC FIELD ENERGY PROPAGATION

(71) Applicant: Xuegang Xin, Guangdong (CN)

(72) Inventor: Xuegang Xin, Guangdong (CN)

( * ) Notice: Subject to any disclaimer, the term of this patent is extended or adjusted under 35 U.S.C. 154(b) by 307 days.

(21) Appl. No.: 16/311,043

(22) PCT Filed: May 8, 2017

(86) PCT No.: PCT/CN2017/083447
§ 371 (c)(1),
(2) Date: Dec. 18, 2018

(87) PCT Pub. No.: WO2017/219765
PCT Pub. Date: Dec. 28, 2017

(65) Prior Publication Data
US 2019/0150782 A1    May 23, 2019

(30) Foreign Application Priority Data

Jun. 23, 2016 (CN) .......................... 201610472784.7
May 8, 2017 (WO) ................. PCT/CN2017/083447

(51) Int. Cl.
*A61B 5/055* (2006.01)
*G01R 33/54* (2006.01)
*G01R 33/28* (2006.01)
*A61B 6/03* (2006.01)
*G01R 33/24* (2006.01)

(52) U.S. Cl.
CPC ............... *A61B 5/055* (2013.01); *A61B 6/03* (2013.01); *G01R 33/246* (2013.01); *G01R 33/288* (2013.01); *G01R 33/54* (2013.01); *G06T 2207/10088* (2013.01)

(58) Field of Classification Search
CPC .... G01R 33/54; G01R 33/246; G01R 33/288; G06T 2207/10088; A61B 5/055
See application file for complete search history.

(56) References Cited

FOREIGN PATENT DOCUMENTS

CN         2006064002         3/2006

*Primary Examiner* — Jason M Ip

(57) ABSTRACT

A method for solving the electrical property distribution and local specific absorption rate of tissue from the view of electromagnetic field energy propagation, comprising the steps of: (1) calculating the total energy emitted by a nuclear magnetic resonance radio-frequency emission point, and subtracting the energy reflected back by a system therefrom to obtain the total energy of an electromagnetic field existing in human tissue; (2) according to a $B_1$ mapping technique, obtaining an amplitude distribution of a magnetic field, i.e. $B_1+$ field, produced through radio-frequency emission, and further obtaining the energy of the $B_1^+$ field; and at the same time, obtaining the energy of an electric field according to the electro-magnetic mutual production theory based on Maxwell's equations.

5 Claims, 2 Drawing Sheets

Electric Field Energy

Magnetic Field Energy

Heat Loss

Total Energy

METHOD FOR SOLVING ELECTRICAL PROPERTY DISTRIBUTION AND LOCAL SPECIFIC ABSORPTION RATE OF TISSUE FROM VIEW OF ELECTROMAGNETIC FIELD ENERGY PROPAGATION

TECHNICAL FIELD OF THE INVENTION

The present invention relates to the technical field of magnetic resonance imaging, and more particularly, to a method for solving the electrical property distribution and local specific absorption rate of tissue from the view of electromagnetic field energy propagation.

BACKGROUND OF THE INVENTION

Electrical properties (EPs) are also called dielectric properties, and refer particularly to the electrical conductivity σ and permittivity ε of tissue. These parameters can directly reflect the physiological and pathological states of tissue. Research shows that the electrical properties of a normal tissue differ much from that of a tumor tissue. Therefore, through comparing the EPs distribution diagram of a living tissue and that of a normal tissue, the physiological and pathological states of tissue can be known, which has a great importance in the diagnosis of diseases and early detection of tumors.

During the imaging process, when a magnetic field acts on human tissues, the living tissue starts absorbing the radio-frequency energy. The specific absorption rate increases along with the increase of the intensity of the main magnetic field. When the radio-frequency energy absorbed by the tissue exceeds the body's self-regulating capacity, local burns or even body temperature regulation disorders can occur, resulting in a series of complications such as electrolyte metabolism disorders and nervous system disorders, etc. Due to the above, the quantitative measurement of the local specific absorption rate (Local SAR) of a whole body's tissues in an ultrahigh-field magnetic resonance imaging (MM) process has a high clinical value.

Recently, the research of a magnetic resonance human-tissue electrical property tomography (MR EPT) has attracted scientists' attentions. Such research combines a Bimapping technique, and the result can be derived through Maxwell's equations. Until now, remarkable achievements have been made under magnetic resonance at the intensity of 3T and 7T. These achievements include the following:

In 2009, the magnetic resonance human-tissue electrical property tomography (MR EPT) at the intensity of 3T was studied systematically by Katscher et al. (hereinafter Katscher) of Philips' European R&D center. According to Katscher's research, a z-direction component of the intensity vector under a RF magnetic field is ignored, only using other two components for analyzing and solving the electric conductivity and permittivity at each location of the tissue. This research achieves a measurement of the electric conductivity and permittivity of living tissue in a birdcage coil, greatly promoting the development of the magnetic resonance human-tissue electrical property tomography (MR EPT) at the intensity of 3T. Soon afterwards, in 2011, Voigt et al. of Germany's Karlsruhe Biomedical Engineering Institute made a assumption on the amplitude and phase of the radio-frequency field at the intensity of 3T on the basis of Katscher's research. According to this assumption, a phase-based method for solving the electrical conductivity and a magnetic-field-amplitude-based method for solving the permittivity were proposed. After comparing Voigt's MR EPT algorithm based on the aforesaid assumption with Katscher's, it was found that the difference between their measuring results was within 10% (it didn't mean that the error between actual values was also within 10%). However, as the algorithm was greatly simplified, the MR EPT method took one step further towards the practical clinical application. Further, on a solid basis of Voigt's research, Bulumulla et al. of GE's global R&D center successfully realized the tomography of the permittivity based on the RF field amplitude and the electrical conductivity based on the RF field phase of tissue in magnetic resonance at the intensity of 3T, and further simplified the MR EPT algorithm. In 2013, by utilizing the characteristic that the tissue of a human brain was approximately symmetrical about the left and right, Bin He et al. (hereinafter Bin He) of University of Minnesota raised an assumption that the amplitude of the RF emitting magnetic field roughly equaled that of the RF receiving magnetic field. Through extracting the proton density distribution of the whole brain from the signals received by RF multi-coil channels, calculating the amplitude and phase of each channel's receiving field, and combining each channel's emitting magnetic field obtained through adopting 7T ultrahigh-field multi-channel RF coil Bimapping technique, Bin He realized the non-invasive EPs tomography of human brain tissues in magnetic resonance at the intensity of 7T according to the MR EPT second-order differential algorithm. Moreover, aiming at the problem that the phases of the multi-channel coil emitting and receiving fields cannot be directly measured in magnetic resonance at the intensity of 7T, Sodickson et al. (hereinafter Sodickson) of Bernald and Irene Schewartz Center for Biomedical Imaging, New York University, proposed a method for solving the phase of each coil channel by utilizing the Local Maxwell Tomography (LMT). Sodickson separated the real part and the imaginary part on the two sides of the Maxwell's equation of each channel, thereby obtaining two groups of different equations. Theoretically, unknown quantities including the proton density distribution, the phase of each emitting channel, and the phase of each receiving channel can be solved by using the measurement data of more than five groups of emitting and receiving coil channels, and the tissue's EPs distribution of each pixel point of an imaging area can be obtained further according to the MR EPT second-order differential algorithm.

Meanwhile, along the increase of the $B_0$ field, the distribution measurement of radio-frequency hot spots of a living tissue becomes a problem that needs to be solved urgently. As none of the prior solutions can perfectly solve it, relevant researches in worldwide become very active. In the prior art, there're mainly two methods for quantitatively determining the distribution of radio-frequency hot spots, wherein one is the simulating calculation method based on a human body electromagnetic model, and the other is the MR scanning calculation method based on the linear magnetic resonance human-tissue electrical property tomography (MR EPT). The simulating calculation method based on a human body electromagnetic model is to dispose a human body electromagnetic model under a specific MR radio-frequency coil, and calculate the distribution of $B_1$ field in human tissues after certain radio-frequency scanning parameters are set. By referring to complex electromagnetic parameters of an isolated issue, the distribution of the radio-frequency hot spots of a living tissue can be obtained. Regarding the MR scanning calculation method, Katscher proposed a method for determining the electrical conductivity and the local radio-frequency hot spots of tissue in 2009, and Voigt also proposed a method for linearly measuring the complex dielectric parameters of a brain tissue in 2011, namely, the linear MR EPT method. Based on these, a radio-frequency hot-spot distribution calculation method of the living tissue was proposed in 2012. However, this method cannot be applied to a whole human body, for it is only verified in the living MR scanning of a brain, and the calculation error is about 20%, failing to achieve a high calculation accuracy. Bin He's research on measuring the complex dielectric parameters of a brain tissue at the intensity of 7T was reported in 2013, providing great support on further calculating the distribution of radio-frequency hot spots by using MR EPT technology.

The traditional MR EPT technology has the following shortcomings: first, the calculation process and the reconstruction result are seriously influenced by noise; second, the problem relating to the imaging errors existing at the junction of different tissues cannot be solved; third, the imaging resolution is very poor. Reasons causing the aforesaid problems include: first, the traditional MR EPT technology adopts an approximate algorithm, assuming that the gradient of the complex electrical properties of tissue is zero; second, as the reconstruction core algorithm is based on the second-order differential algorithm of Maxwell's equations, the noise in the calculation process can be amplified, making the calculation result be sensitive to the noise; third, the traditional calculation process needs both the amplitude and phase information of a $B_1^+$ field, whereas the phase information cannot be measured but estimated, causing an increase of EPT reconstruction errors based on the $B_1^{+\,field}$.

Regarding methods for solving the local specific absorption rate (Local SAR), the traditional simulation method for calculating the radio-frequency hot-spot distribution based on a human body electromagnetic model is severely limited by the huge workload of establishing an individual patient's whole-body electromagnetic model. Thus, a universal human body electromagnetic model is commonly adopted in practical application, resulting the failure of measuring the differences among individuals. Moreover, when calculating the electromagnetic model, the complex dielectric parameters of an isolated tissue are usually referenced. Therefore, a certain difference exists between the complex dielectric parameters of the isolated tissue and that of a living tissue, which also causes the deviation of calculation results. As for the MR scanning method for calculating the radio-frequency hot-spot distribution based on the linear MR EPT, the variation of the complex dielectric parameters in the target region to be measured is required to be far smaller than that of an electric field. For complex dielectric parameters of tissues in the whole body are quite different, this requirement cannot be satisfied for a whole body's tissues but only for brain tissues consisted primarily of soft tissues.

In conclusion, it's urgent for those skilled in this field to solve the prior technical problems by providing a method for solving the electrical property distribution and local specific absorption rate of tissue from the view of electromagnetic field energy propagation.

SUMMARY OF THE INVENTION

The purpose of the present invention is to solve the shortcomings in the prior art by providing a method for solving the electrical property distribution and local specific absorption rate of tissue from the view of electromagnetic field energy propagation, which has the characteristics of simple calculation and precise results.

To achieve the above purpose, the present invention adopts the following technical solution:

The present invention provides a method for solving the electrical property distribution and local specific absorption rate of tissue from the view of electromagnetic field energy propagation, which is based on the following physical fact: the electromagnetic energy is transmitted from the periphery into the human body under the action of the radio-frequency coils; the electric-field energy and the magnetic-field energy are alternately converted, and the energies cannot be abruptly changed; during the conversion of the energies, a part of the electric-field energy is converted into heart energy and consumed.

The calculating formula of the total energy of the magnetic field of the nuclear magnetic resonance radio-frequency emission points is the following:

$$W = \frac{1}{2\mu}\omega B \cdot B^* + \frac{1}{2}\omega\varepsilon E \cdot E^* + \frac{1}{2}\sigma E \cdot E^*, \quad \text{Formula 1}$$

wherein $\omega$ represents the angular frequency, $\mu$ represents the magnetic conductivity, $\varepsilon$ represents the permittivity, $\sigma$ represents the electrical conductivity, B represents the magnetic induction intensity, E represents the electric field intensity, * represents taking a complex conjugate, $$\frac{1}{2\mu}\omega B \cdot B^*$$

represents the energy storage of the magnetic field, $1/2\omega\varepsilon E \cdot E^*$ represents the energy storage of the electric field, and $1/2\sigma E \cdot E^*$ represents the joule heat loss.

The present invention provides a method for solving the electrical property distribution of tissue from the view of electromagnetic field energy propagation, comprising the steps of:

(1) According to the power value and the radio-frequency emission time of the radio-frequency power amplifier as well as the working efficiency of system, calculating the total energy emitted by a nuclear magnetic resonance radio-frequency emission point, and subtracting the energy reflected back by a system therefrom to obtain the total energy of an electromagnetic field existing in human tissue;

(2) According to a $B_1$ mapping technique, obtaining an amplitude distribution of a magnetic field, i.e. $B_1+$ field, produced through radio-frequency emission at each point in human body, and further obtaining the energy of the $B_1^+$ field at each point in human body according to formula $$\frac{1}{2\mu}\omega B \cdot B^*;$$

and at the same time, obtaining the energy of an electric field according to the electro-magnetic mutual production theory based on Maxwell's equations;

(3) In the process that energy is transmitted from an outer circle to an inner circle, the total energy being continuously reduced due to the loss of heat energy, the energy reduced between corresponding points in each circle being equivalent to the energy difference of the $B_1^+$ field between the corresponding points of the two circles, namely:

$$\frac{1}{2\mu}\omega B \cdot B^*;$$

wherein $B_{out}$ represents the magnetic induction intensity of an outer circle, $B_{in}$ represents the magnetic induction intensity of an inner circle, and $E_{out}$ represents the electric field intensity of an outer circle, wherein $B_{in}$ and $B_{out}$ can be obtained through the $B_1$ Mapping technique; and, the magnetic field energy of the inner circle being converted into the electric field energy of the outer circle, namely:

$$\frac{1}{2}\omega \varepsilon E_{out} \cdot E^*_{out} = \frac{1}{2\mu}\omega B_{in} \cdot B^*_{in};$$ Formula 3 dividing formula 2 by formula 3, thereby obtaining a tangent value of a loss angle, wherein the tangent value of a loss angle is the ratio of the electrical conductivity of the tissue at a position where outer circle points are located to a relative dielectric constant, wherein the relative dielectric constant is the product of the permittivity and the angular frequency, wherein the formula of the tangent value of a loss angle is $$\frac{\sigma}{\omega \varepsilon};$$

subsequently, obtaining the ratio $$\frac{\sigma}{\omega \varepsilon}$$

of the electrical conductivity of tissue in an imaging area to the relative dielectric constant through the above calculations.

The present invention also provides a method for solving the local specific absorption rate of tissue from the view of electromagnetic field energy propagation, which is based on the following physical fact: the electromagnetic energy is transmitted from the periphery into the human body under the action of the radio-frequency coils; the electric-field energy and the magnetic-field energy are alternately converted, and the energies cannot be abruptly changed; during the conversion of the energies, a part of the electric-field energy is converted into heart energy and consumed.

The calculating formula of the total energy of the magnetic field of the nuclear magnetic resonance radio-frequency emission points is the following:

$$W = \frac{1}{2\mu}\omega B \cdot B^* + \frac{1}{2}\omega \varepsilon E \cdot E^* + \frac{1}{2}\sigma E \cdot E^*,$$ Formula 1 wherein $\omega$ represents the angular frequency, $\mu$ represents the magnetic conductivity, $\varepsilon$ represents the permittivity, $\sigma$ represents the electrical conductivity, B represents the magnetic induction intensity, E represents the electric field intensity, * represents taking a complex conjugate, $$\frac{1}{2\mu}\omega B \cdot B^*$$

represents the energy storage of the magnetic field, $1/2\omega \varepsilon E \cdot E^*$ represents the energy storage of the electric field, and $1/2\sigma E \cdot E^*$ represents the joule heat loss.

The method for solving the local specific absorption rate of tissue from the view of electromagnetic field energy propagation, comprising the steps of:

(1) According to the power value and the radio-frequency emission time of the radio-frequency power amplifier as well as the working efficiency of system, calculating the total energy emitted by a nuclear magnetic resonance radio-frequency emission point, and subtracting the energy reflected back by a system therefrom to obtain the total energy of an electromagnetic field existing in human tissue, wherein the energy reflected back can be obtained through measurement;

(2) According to a $B_1$ mapping technique, obtaining an amplitude distribution of a magnetic field, i.e. $B_1+$ field, produced through radio-frequency emission at each point in human body, and further obtaining the energy of the $B_1^+$ field at each point in human body according to formula $$\frac{1}{2\mu}\omega B \cdot B^*;$$

and at the same time, obtaining the energy of an electric field according to the electro-magnetic mutual production theory based on Maxwell's equations;

(3) In the process that energy is transmitted from an outer circle to an inner circle, the total energy being continuously reduced due to the loss of heat energy, the energy reduced between corresponding points in each circle being equivalent to the energy difference of the $B_1^+$ field between the corresponding points of the two circles, namely:

$$\frac{1}{2\mu}\omega B_{out} \cdot B^*_{out} - \frac{1}{2\mu}\omega B_{in} \cdot B^*_{in} = \frac{1}{2}\sigma E_{out} \cdot E^*_{out};$$ Formula 2 and the magnetic field energy of the inner circle being converted into the electric field energy of the outer circle, namely:

$$\frac{1}{2}\omega \varepsilon E_{out} \cdot E^*_{out} = \frac{1}{2\mu}\omega B_{in} \cdot B^*_{in};$$ Formula 3 and for the outer circle:

$$\frac{1}{2}\omega \varepsilon E_{out} \cdot E^*_{out} + \frac{1}{2}\sigma E_{out} \cdot E^*_{out} = \frac{1}{2\mu}\omega B_{out} \cdot B^*_{out},$$ Formula 4 wherein $B_{out}$ represents the magnetic induction intensity of an outer circle, $B_{in}$ represents the magnetic induction intensity of an inner circle, and $E_{out}$ represents the electric field intensity of an outer circle, wherein $B_{in}$ and $B_{out}$ can be obtained through the $B_1$ Mapping technique;

by comparing the difference in the total energy of the electromagnetic field between each point in an inner circle and an outer circle, namely, $$\left(\frac{1}{2\mu}\omega(B_{out} \cdot B_{out}^* - B_{in} \cdot B_{in}^*)\right),$$

obtaining the values of heat energy loss of each point in each circle, namely, 1/2σE·E* of each point in each circle, and performing calculation to obtain a local specific absorption rate (Local SAR) of each point in each circle by using the tissue density ρ (a given value) of each point in human tissue, namely, $$\text{Local } SAR = \frac{1}{2\rho}\sigma E \cdot E^*.$$

Compared with the prior art, the present invention has the following advantages:

According to the method for solving local specific absorption rate of tissue of the present invention, the EPs are solved from a view of the energy propagation and distribution of the magnetic resonance radio-frequency emitting electromagnetic field. The calculation process uses only the amplitude information of the radio-frequency field that can be directly measured, meaning that the phase information of the radio-frequency field that cannot be directly measured is no longer needed, and the second-order differential calculation based on Maxwell's equations can be avoided. Thus, the precision of results can be effectively improved.

The present invention provides a method for solving the electrical property distribution and local specific absorption rate of tissue from a new view—the electromagnetic field energy propagation, which has the characteristics of simple calculation and precise results.

BRIEF DESCRIPTION OF THE DRAWINGS

To clearly expound the technical solution of the present invention, the drawings and embodiments are hereinafter combined to illustrate the present invention. Obviously, the drawings are merely some embodiments of the present invention and those skilled in the art can associate themselves with other drawings without paying creative labor.

DETAILED DESCRIPTION OF THE INVENTION

Drawings and detailed embodiments are combined hereinafter to elaborate the technical principles of the present invention.

Embodiment 1

The present invention provides a method for solving the electrical property distribution of tissue from the view of electromagnetic field energy propagation, which is based on the following physical fact: the electromagnetic energy is transmitted from the periphery into the human body under the action of the radio-frequency coils; the electric-field energy and the magnetic-field energy are alternately converted, and the energies cannot be abruptly changed; during the conversion of the energies, a part of the electric-field energy is converted into heart energy and consumed.

The calculating formula of the total energy of the magnetic field of the nuclear magnetic resonance radio-frequency emission points is the following:

$$W = \frac{1}{2\mu}\omega B \cdot B^* + \frac{1}{2}\omega \varepsilon E \cdot E^* + \frac{1}{2}\sigma E \cdot E^*, \quad \text{Formula 1}$$

wherein ω represents the angular frequency, μ represents the magnetic conductivity, ε represents the permittivity, σ represents the electrical conductivity, B represents the magnetic induction intensity, E represents the electric field intensity, * represents taking a complex conjugate, $$\frac{1}{2\mu}\omega B \cdot B^*$$

represents the energy storage of the magnetic field, 1/2ωεE·E* represents the energy storage of the electric field, and 1/2σE·E* represents the joule heat loss.

The method for solving the electrical property distribution of tissue from the view of electromagnetic field energy propagation, comprising the steps of:

(1) According to the power value and the radio-frequency emission time of the radio-frequency power amplifier as well as the working efficiency of system, calculating the total energy emitted by a nuclear magnetic resonance radio-frequency emission point, and subtracting the energy reflected back by a system therefrom to obtain the total energy of an electromagnetic field existing in human tissue;

(2) According to a $B_1$ mapping technique, obtaining an amplitude distribution of a magnetic field, i.e. $B_1^+$ field, produced through radio-frequency emission at each point in human body, and further obtaining the energy of the $B_1^+$ field at each point in human body according to formula $$\frac{1}{2\mu}\omega B \cdot B^*;$$

and at the same time, obtaining the energy of an electric field according to the electro-magnetic mutual production theory based on Maxwell's equations;

(3) In the process that energy is transmitted from an outer circle to an inner circle, the total energy being continuously reduced due to the loss of heat energy, the energy reduced between corresponding points in each circle being equivalent to the energy difference of the $B_1^+$ field between the corresponding points of the two circles, namely:

$$\frac{1}{2\mu}\omega B_{out} \cdot B_{out}^* - \frac{1}{2\mu}\omega B_{in} \cdot B_{in}^* = \frac{1}{2}\sigma E_{out} \cdot E_{out}^*; \quad \text{Formula 2}$$

and the magnetic field energy of the inner circle being converted into the electric field energy of the outer circle, namely:

$$\frac{1}{2}\omega\varepsilon E_{out} \cdot E_{out}^* = \frac{1}{2\mu}\omega B_{in} \cdot B_{in}^*; \qquad \text{Formula 3}$$

dividing formula 2 by formula 3, thereby obtaining a tangent value of a loss angle, wherein the tangent value of a loss angle is the ratio of the electrical conductivity of the tissue at a position where outer circle points are located to a relative dielectric constant, wherein the relative dielectric constant is the product of the permittivity and the angular frequency, wherein the formula of the tangent value of a loss angle is $$\frac{\sigma}{\omega\varepsilon};$$

subsequently, obtaining the ratio $$\frac{\sigma}{\omega\varepsilon}$$

of the electrical conductivity of tissue in an imaging area to the relative dielectric constant through the above calculations.

As the value of the dielectric property of human tissue is known, the ratio $$\frac{\sigma}{\omega\varepsilon},$$

namely, the tangent value of a loss angle is also known. By comparing the result of the distribution imaging of the value $$\frac{\sigma}{\omega\varepsilon}$$

obtained from the above calculation with that of a normal tissue, the position where an abnormal value $$\frac{\sigma}{\omega\varepsilon}$$

is located can be found, providing a valuable spatial positioning for the early-stage discovery of diseases, i.e. early-stage cancerous lesions. According to the method of the present invention, the early-stage diagnosis of tumors can be realized by the aid of technical means such as biopsy, achieving a high clinical application value.

According to the method for solving the electrical property distribution of tissue of the present invention, the EPs are solved from a view of the energy propagation and distribution of the magnetic resonance radio-frequency emitting electromagnetic field. The calculation process uses only the amplitude information of the radio-frequency field that can be directly measured, meaning that the phase information of the radio-frequency field that cannot be directly measured is no longer needed, and the second-order differential calculation based on Maxwell's equations can be avoided. Thus, the precision of results can be effectively improved.

In the tradition MR EPT algorithm, when calculating the MR radio-frequency electromagnetic field, the generally adopted method is to assume that the electrical properties of a local tissue are uniform, namely, assuming the gradient of the electrical properties of a local tissue to be zero, and to ignore the cross-sectional component of radio-frequency electric field and the longitudinal axis component of radio-frequency magnetic field, namely, assuming that $E_{x,y}(r) \approx 0$ and $B_z(r) \approx 0$. The objective of the traditional MR EPT algorithm is to obtain a simplified approximate calculation formula of the EPs, thereby forming an algorithmic theory thereof, for instance, Voigt's solving method based on the permittivity of the amplitude of radio-frequency magnetic field. However, such a simplified method causes an increase of measuring errors in the area with complex electromagnetic boundary condition.

The present invention provides a method for solving Eps from the view of electromagnetic field energy. The calculation process uses only the amplitude information of the magnetic field, making the phase information of radio-frequency field unnecessary. The phase problem remains unsolved in the traditional MR EPT algorithm, for the phase of radio-frequency emitting field cannot be directly measured in engineering by using the traditional MR technology. In the solving process, an approximate solution of the phase distribution is obtained on basis of making many assumptions, resulting in errors of the results. Compared with the prior art, the present invention greatly improves the precision of results while avoiding the second-order differential calculation based on Maxwell's equations.

Embodiment 2

The present invention provides a method for solving the local specific absorption rate of tissue from of electromagnetic field energy propagation, which is based on the following physical fact: the electromagnetic energy is transmitted from the periphery into the human body under the action of the radio-frequency coils; the electric-field energy and the magnetic-field energy are alternately converted, and the energies cannot be abruptly changed; during the conversion of the energies, a part of the electric-field energy is converted into heart energy and consumed.

The calculating formula of the total energy of the magnetic field of the nuclear magnetic resonance radio-frequency emission points is the following:

$$W = \frac{1}{2\mu}\omega B \cdot B^* + \frac{1}{2}\omega\varepsilon E \cdot E^* + \frac{1}{2}\sigma E \cdot E^*, \qquad \text{Formula 1}$$

wherein ω represents the angular frequency, μ represents the magnetic conductivity, ε represents the permittivity, σ represents the electrical conductivity, B represents the magnetic induction intensity, E represents the electric field intensity, * represents taking a complex conjugate, $$\frac{1}{2\mu}\omega B \cdot B^*$$

represents the energy storage of the magnetic field, $1/2\omega\varepsilon E \cdot E^*$ represents the energy storage of the electric field, and $1/2\sigma E \cdot E^*$ represents the joule heat loss.

The method for solving the local specific absorption rate of tissue from the view of electromagnetic field energy propagation, comprising the steps of:

(1) According to the power value and the radio-frequency emission time of the radio-frequency power amplifier as well as the working efficiency of system, calculating the total energy emitted by a nuclear magnetic resonance radio-frequency emission point, and subtracting the energy reflected back by a system therefrom to obtain the total energy of an electromagnetic field existing in human tissue, wherein the energy reflected back can be obtained through measurement;

(2) According to a $B_1$ mapping technique, obtaining an amplitude distribution of a magnetic field, i.e. $B_1+$ field, produced through radio-frequency emission at each point in human body, and further obtaining the energy of the $B_1^+$ field at each point in human body according to formula $$\frac{1}{2\mu}\omega B \cdot B^*;$$

and at the same time, obtaining the energy of an electric field according to the electro-magnetic mutual production theory based on Maxwell's equations;

(3) In the process that energy is transmitted from an outer circle to an inner circle, the total energy being continuously reduced due to the loss of heat energy, the energy reduced between corresponding points in each circle being equivalent to the energy difference of the $B_1^+$ field between the corresponding points of the two circles, namely:

$$\frac{1}{2\mu}\omega B_{out} \cdot B_{out}^* - \frac{1}{2\mu}\omega B_{in} \cdot B_{in}^* = \frac{1}{2}\sigma E_{out} \cdot E_{out}^*; \quad \text{Formula 2}$$

and the magnetic field energy of the inner circle being converted into the electric field energy of the outer circle, namely:

$$\frac{1}{2}\omega\varepsilon E_{out} \cdot E_{out}^* = \frac{1}{2\mu}\omega B_{in} \cdot B_{in}^*; \quad \text{Formula 3}$$

and for the outer circle:

$$\frac{1}{2}\omega\varepsilon E_{out} \cdot E_{out}^* + \frac{1}{2}\sigma E_{out} \cdot E_{out}^* = \frac{1}{2\mu}\omega B_{out} \cdot B_{out}^*, \quad \text{Formula 4}$$

wherein $B_{out}$ represents the magnetic induction intensity of an outer circle, $B_{in}$ represents the magnetic induction intensity of an inner circle, and $E_{out}$ represents the electric field intensity of an outer circle, wherein $B_{in}$ and $B_{out}$ can be obtained through the $B_1$ Mapping technique;

by comparing the difference in the total energy of the electromagnetic field between each point in an inner circle and an outer circle, namely, $$\left(\frac{1}{2\mu}\omega(B_{out} \cdot B_{out}^* - B_{in} \cdot B_{in}^*)\right),$$

obtaining the values of heat energy loss of each point in each circle, namely, $1/2\sigma E \cdot E^*$ of each point in each circle, and performing calculation to obtain a local specific absorption rate (Local SAR) of each point in each circle by using the tissue density $\rho$ (a given value) of each point in human tissue, namely, $$\text{Local } SAR = \frac{1}{2\rho}\sigma E \cdot E^*.$$

According to the method for solving local specific absorption rate of tissue of the present invention, the EPs are solved from a view of the energy propagation and distribution of the magnetic resonance radio-frequency emitting electromagnetic field. The calculation process uses only the amplitude information of the radio-frequency field that can be directly measured, meaning that the phase information of the radio-frequency field that cannot be directly measured is no longer needed, and the second-order differential calculation based on Maxwell's equations can be avoided. Thus, the precision of results can be effectively improved. By combining the density and electric field amplitude of tissue on the basis of EPs distribution of tissue, the distribution of local SAR can be obtained according to the Local SAR calculation formula.

The present invention provides a method for solving the electrical property distribution and local specific absorption rate of tissue from a new view—the electromagnetic field energy propagation, which has the characteristics of simple calculation and precise results.

Embodiment 3

The accuracy of the present invention is verified by performing simulations, phantom experiments, and actual measurements of human bodies, etc.

1) Simulations

Figure 1:
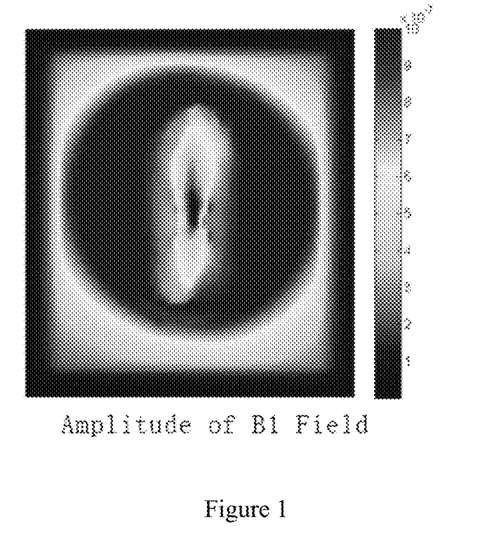
FIG. 1 is a distribution diagram of the amplitude and phase of the radio-frequency field in a simulation of embodiment 3 of the present invention.
Figure 2:
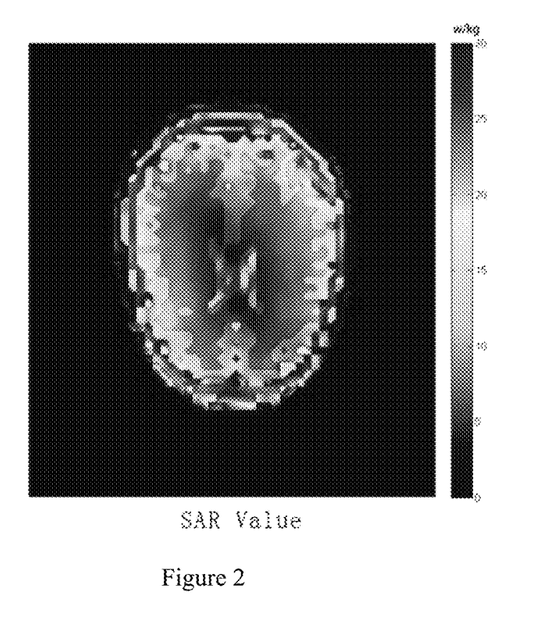
FIG. 2 is a distribution diagram of SAR values obtained from a simulation of embodiment 3 of the present invention.
Figure 3:
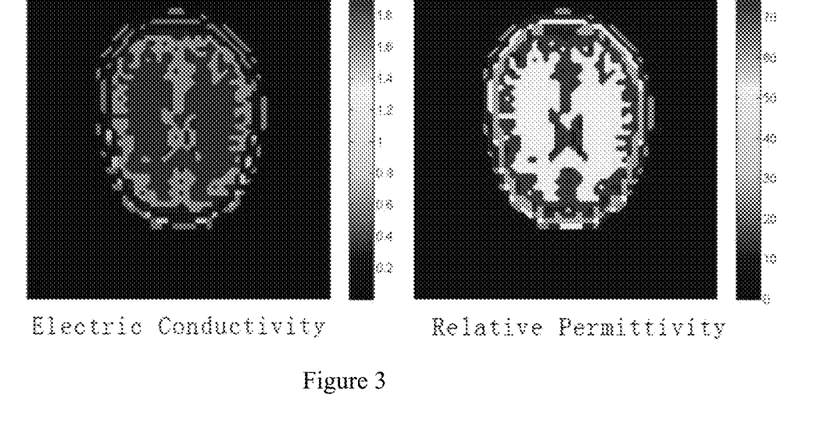
FIG. 3 are distribution diagrams of the electric conductivity and relative permittivity calculated out from a simulation of embodiment 3 of the present invention.
Figure 4:
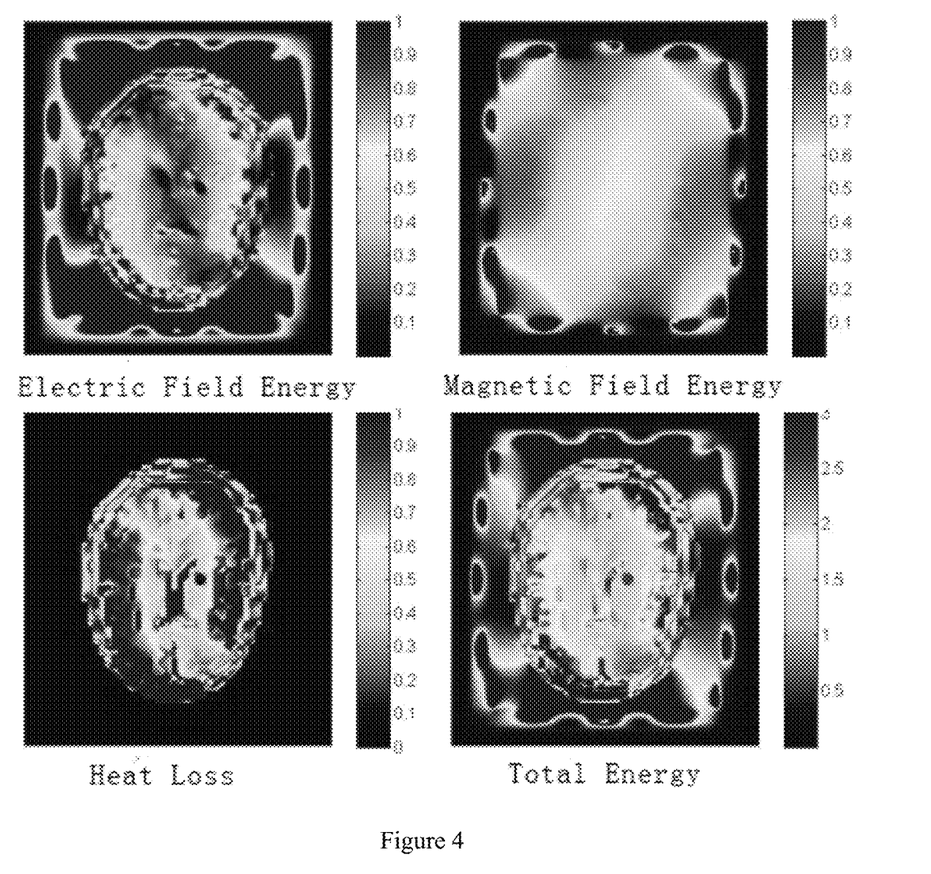
FIG. 4 are distribution diagrams of the electric field energy, magnetic field energy, heat loss and total energy in a simulation of embodiment 3 of the present invention.

By using SEMCAD software, and setting the frequency of the nuclear magnetic resonance to be 128 MHZ, a 16-channel high-pass birdcage coil is established. Subsequently, a DUKE head model is placed into the birdcage coil. As shown in FIG. 1, the distribution of the head radio-frequency field, i.e. $B_1+$ field, is obtained. After a propagation model of the magnetic field from outside to inside is established, the obtained B is put into the formula 2, thereby obtaining a heat loss value of tissue. As the value of tissue density is known, after it is put into the solution formula of Local SAR, the distribution of Local SAR can be determined (as shown in FIG. 2). The permittivity of tissue can be calculated out through formulas 1 and 4, and the electric conductivity of a corresponding point can be calculated out according to the tangent value of a loss angle (as shown in FIG. 3). FIG. 4 are distribution diagrams of the electric field energy, magnetic field energy, heat loss and total energy in the simulation of embodiment 3 of the present invention.

2) Phantom Experiments

Through adopting various dielectric materials capable of simulating the electrical properties of different tissues, and filling a cavity having a specific structure, an electromagnetic boundary condition resembling the interface of different tissues of a human body can be formed, and a special phantom can be made. By adopting different scanning sequences in magnetic resonance at the intensity of 3T, corresponding images can be obtained, and by using the $B_1$ Mapping technique, the amplitude $|B_1^+|$ of the radio-frequency field can be obtained. Subsequently, after combining the energy field of the nuclear magnetic resonance, the electrical properties and the local specific absorption ratio can be solved.

3) Actual Measurements of Human Bodies

After the accuracy of the electrical properties obtained based on the energy field of the nuclear magnetic resonance through simulations and phantom experiments is verified, actual measurements of human bodies are carried out among clinical volunteers consisted of healthy people and tumor patients.

According to the simulations, phantom experiments and actual measurements of human bodies, it is proved that the method of the present invention can simply and precisely obtain the electrical property distribution and local specific absorption rate of tissue.

The present invention provides a method for solving EPs from the view of electromagnetic field energy. The calculation process uses only the amplitude information of the magnetic field, making the phase information of radio-frequency field unnecessary. The phase problem remains unsolved in the traditional MR EPT algorithm, for the phase of radio-frequency emitting field cannot be directly measured in engineering by using the traditional MR technology. In the solving process, an approximate solution of the phase distribution is obtained on basis of making many assumptions, resulting in errors of the results. Compared with the prior art, the present invention greatly improves the precision of results while avoiding the second-order differential calculation based on Maxwell's equations. Thus, the precision of results can be greatly improved.

By combining the density, electric field amplitude and electric conductivity of tissue on the basis of EPs distribution of tissue, the distribution of Local SAR can be obtained according to the Local SAR calculation formula.

The present invention provides a method for solving the electrical property distribution and local specific absorption rate of tissue from a new view the electromagnetic field energy propagation, which has the characteristics of simple calculation and precise results.

The description of above embodiments allows those skilled in the art to realize or use the present invention. Without departing from the spirit and essence of the present invention, those skilled in the art can combine, change or modify correspondingly according to the present invention. Therefore, the protective range of the present invention should not be limited to the embodiments above but conform to the widest protective range which is consistent with the principles and innovative characteristics of the present invention. Although some special terms are used in the description of the present invention, the scope of the invention should not necessarily be limited by this description. The scope of the present invention is defined by the claims.

The invention claimed is:

1. A method for imaging tissue using a magnetic resonance imaging (MRI) device comprising:
   (a) transmitting electromagnetic energy into a human body using radio-frequency coils; and
   (b) alternatively converting the electric-field energy and the magnetic-field energy without abruptly changing the electric-field energy and the magnetic-field energy; wherein during conversion from an electric-field energy to a magnetic-field energy, a part of the electric-field energy is converted into heat energy and consumed, and wherein a total energy of a magnetic field of nuclear magnetic resonance radio-frequency emission points is calculated by the MRI device using the following Formula 1:

$$W = \frac{1}{2\mu}\omega B \cdot B^* + \frac{1}{2}\omega\varepsilon E \cdot E^* + \frac{1}{2}\sigma E \cdot E^*,$$

wherein $\omega$ represents angular frequency, $\mu$ represents magnetic conductivity, $\varepsilon$ represents permittivity, $\sigma$ represents electrical conductivity, B represents magnetic induction intensity, E represents electric field intensity, * represents taking a complex conjugate, $$\frac{1}{2\mu}\omega B \cdot B^*$$

represents energy storage of the magnetic field, $$\frac{1}{2}\omega\varepsilon E \cdot E^*$$

represents energy storage of the electric field, and $$\frac{1}{2}\sigma E \cdot E^*$$

represents joule heat loss.

2. The method of claim 1, wherein the MRI device outputs the total energy emitted by a nuclear magnetic resonance radio-frequency emission point and subtracting an energy reflected back by a system to obtain a total energy of an electromagnetic field existing in a human tissue.

3. The method of claim 2, wherein the MRI device obtains an amplitude distribution of a $B_1^\pm$ field, produced through radio-frequency emission at each point in a human body and obtains an energy of the $B_1^+$ field at each point in the human body according to Formula $$\frac{1}{2\mu}\omega B \cdot B^*;$$

while obtaining the energy of an electric field according to Maxwell's electro-magnetic mutual production theory.

4. The method of claim 3, wherein the MRI device calculates an energy that is transmitted from an outer circle to an inner circle, the total energy being continuously reduced due to the loss of heat energy, the energy reduced between corresponding points in each circle being equivalent to an energy difference of the $B_1^+$ field between the corresponding points of the two circles as described in the following Formula 2:

$$\frac{1}{2\mu}\omega B_{out} \cdot B_{out}^* - \frac{1}{2\mu}\omega B_{in} \cdot B_{in}^* = \frac{1}{2}\sigma E_{out} \cdot E_{out}^*;$$

wherein $B_{out}$ represents a magnetic induction intensity of an outer circle, $B_{in}$ represents a magnetic induction intensity of an inner circle, and $E_{out}$ represents an electric field intensity of an outer circle, wherein $B_{in}$ and $B_{out}$ can be obtained through a $B_1$ Mapping technique; and, the magnetic field energy of the inner circle being converted into the electric field energy of the outer circle represented by Formula 3:

$$\frac{1}{2}\omega\varepsilon E_{out} \cdot E_{out}^* = \frac{1}{2\mu}\omega B_{in} \cdot B_{in}^*$$

and divides Formula 2 by Formula 3, thereby obtaining a tangent value of a loss angle, wherein the tangent value of a loss angle is a ratio of an electrical conductivity of the tissue at a position where outer circle points are located to a relative dielectric constant, wherein the relative dielectric constant is the product of the permittivity and the angular frequency, wherein the formula of the tangent value of a loss angle is $$\frac{\sigma}{\omega\varepsilon};$$

subsequently, obtaining the ratio $$\frac{\sigma}{\omega\varepsilon}$$

of the electrical conductivity of tissue in an imaging area to the relative dielectric constant.

5. The method of claim 3, wherein the MRI device calculates the energy that is transmitted from an outer circle to an inner circle, the total energy being continuously reduced due to a loss of heat energy, the energy reduced between corresponding points in each circle being equivalent to an energy difference of the $B_1^+$ field between the corresponding points of the two circles, namely:

$$\frac{1}{2\mu}\omega B_{out} \cdot B_{out}^* - \frac{1}{2\mu}\omega B_{in} \cdot B_{in}^* = \frac{1}{2}\sigma E_{out} \cdot E_{out}^*; \quad \text{Formula 2}$$

and the magnetic field energy of the inner circle being converted into the electric field energy of the outer circle, namely:

$$\frac{1}{2}\omega\varepsilon E_{out} \cdot E_{out}^* = \frac{1}{2\mu}\omega B_{in} \cdot B_{in}^*; \quad \text{Formula 3}$$

and for the outer circle:

$$\frac{1}{2}\omega\varepsilon E_{out} \cdot E_{out}^* + \frac{1}{2}\sigma E_{out} \cdot E_{out}^* = \frac{1}{2\mu}\omega B_{out} \cdot B_{out}^*, \quad \text{Formula 4}$$

wherein $B_{out}$ represents a magnetic induction intensity of an outer circle, $B_{in}$ represents a magnetic induction intensity of an inner circle, and $E_{out}$ represents an electric field intensity of an outer circle, wherein $B_{in}$ and $B_{out}$ can be obtained through a $B_1$ Mapping technique, wherein the MRI device compares a difference in the total energy of the electromagnetic field between each point in an inner circle and an outer circle, namely, $$\left(\frac{1}{2\mu}\omega(B_{out} \cdot B_{out}^* - B_{in} \cdot B_{in}^*)\right),$$

obtaining values of heat energy loss of each point in each circle, namely, $1/2\sigma E \cdot E^*$ of each point in each circle, and calculates a local specific absorption rate of each point in each circle by using the tissue density $\rho$ of each point in human tissue, namely, $$\text{Local } SAR = \frac{1}{2\rho}.$$

\* \* \* \* \*